United States Patent [19]

Ikeda et al.

[11] Patent Number: 5,399,780
[45] Date of Patent: Mar. 21, 1995

[54] METHOD OF PRODUCING TRIARYLBORANE

[75] Inventors: Yoshihiko Ikeda, Shinnanyo; Takeo Yamane, Yamaguchi; Eiichi Kaji; Kenji Ishimaru, both of Shinnanyo, all of Japan

[73] Assignee: Tosoh Akzo Corporation, Tokyo, Japan

[21] Appl. No.: 141,545

[22] Filed: Oct. 27, 1993

[30] Foreign Application Priority Data

Nov. 2, 1992 [JP] Japan ................... 4-317707

[51] Int. Cl.$^6$ ................................ C07F 5/02
[52] U.S. Cl. ................................ 568/1; 568/6
[58] Field of Search ........................ 568/1, 6

[56] References Cited

U.S. PATENT DOCUMENTS 3,405,179 10/1968 Wowk ..................... 568/1

Primary Examiner—Johann Richter
Assistant Examiner—Michael B. Hydorn
Attorney, Agent, or Firm—Oblon, Spivak, McClelland, Maier, & Neustadt

[57] ABSTRACT

A method of producing a high-purity triarylborane with high yield by reacting, in a solvent inert to the reaction product, a 1.0-8.0 mol/L boron halide solution with a 0.1-3.0 mol/L aryl magnesium halide solution in a straight chain ether solvent, where the molar ratio of aryl magnesium halide to boron trihalide is 3.1-3.5 to 1.0, respectively, and then the straight chain ether solvent is distilled from the reaction mixture. Distillation crystallizes out the halogenated magnesium salt which is produced as a by-product, increasing the recovery rate of the product.

11 Claims, No Drawings

METHOD OF PRODUCING TRIARYLBORANE

BACKGROUND OF THE INVENTION

The present invention relates to a method of producing triarylborane. In more detail, it provides a method to produce a highly pure triarylborane stably in high yield by restricting the range of the molar ratio of arylmagnesium halide to boron halide.

It is known that, by reacting an organic magnesium reactant with a boron trihalide such as boron trifluoride ethyl ether complex, a trialkyl- or and arylborane can be obtained (e.g. Inorg. Synth., 15, 1947, P134).

However, it is stated that, if the reaction is conducted at a molar ratio of arylmagnesium halide to boron trihalide even in amount which is just a little in excess of arylmagnesium halide than 3:1, or if the time for dropwise addition of arylmagnesium halide is too fast, then the production of tetraarylborate becomes high resulting in lower yield of triarylborane. This requires severe production conditions and difficult management of the production process.

Moreover, other production methods of triarylborane include a method wherein phenyl bromide is added to metallic magnesium and boron trifluoride ethyl ether complex and then ultrasonic waves are applied (e.g. J. Org. Chem., 51, 1986, P427), a method of synthesizing triarylborane from phenylmagnesium bromide and trialkyl boric acid ester (e.g. U.S. Pat. No. 3,651,146), a method of reacting phenyl lithium with boron trifluoride ethyl ether complex (e.g. A., 563, 1949, P110), etc.

However, the application of ultrasonic waves is undesirable industrially, the use of trialkyl boric acid ester as a source of boron has a drawback of low yield, and the method of using aryl lithium poses a problem of primary production of tetraarylborate.

As described, conventional methods had the problems of low yield and purity of triarylborane and poor reproducibility.

The inventors investigated extensively on the production conditions of triarylborane through the reaction of boron trihalide with arylmagnesium halide. And, the use levels of boron trihalide and arylmagnesium halide were examined at a molar ratio of 1:3 as described in literature for synthesis. As a result, the inventors have known that, if using the synthetic method described in literature (e.g. Inorg. Synth., 15, 1947, P134), then both the yield and the purity of triarylborane are low and the reproducibility is also poor.

The purpose of the invention is to provide a production method which allows one to improve such drawbacks and to obtain triarylborane in higher yield and higher purity.

As a result of diligent studies, the inventors have found that, by reacting boron trihalide with arylmagnesium halide at 3.1 to 3.5 mol of arylmagnesium halide to 1 mol of boron trihalide, and further by removing the ether type solvent from the reaction mixture, thereby solidifying the halogenated magnesium salt produced as a by-product to release triarylborane enclosed in the magnesium salt, triarylborane can be obtained stably in high yield, leading to the completion of the invention.

SUMMARY OF THE INVENTION

The invention relates to a method of producing triarylborane characterized in that, upon reacting a 0.1 to 8.0 mol/L solution of boron trihalide with a 0.1 to 3.0 mol/L solution of arylmagnesium halide in an organic solvent, where 3.1 to 3.5 mol of arylmagnesium halide is reacted to 1 mol of boron trihalide, afterwards the ether type solvent is removed from the reaction mixture to solidify halogenated magnesium salt produced as a by-product, thus releasing the triarylborane enclosed in the magnesium salt.

DETAILED DESCRIPTION OF THE INVENTION

In following, the invention will be illustrated in detail.

The triarylboranes are boron compounds represented by a general formula (I) of $R_3B$. Here, Rs are identical or different and aryl groups or substituted aryl groups, for example, phenyl, fluorophenyl, chlorophenyl, bromophenyl, methoxyphenyl, tolyl, xylyl, mesityl, biphenyl, naphthyl, pyridyl, trifluorophenyl, pentafluorophenyl, tris(trifluoromethyl) phenyl group, etc. can be mentioned.

As particularly useful compounds among the triarylboranes mentioned above, triphenylborane and tris(pentafluorophenyl) borane are selected. Triphenylboron is useful as a promoter in the hydroboration reaction of olefinic compounds (e.g. U.S. Pat. No. 3,496,215). Also, tris(pentafluorophenyl) borane is useful as an intermediate of catalyst for cationic polymerization (e.g. J. Am. Chem. Soc., 108, 7410, 1986 and J. Am. Chem. Soc., 113, 8570, 1991).

Further, tris(pentafluorophenyl) borane is useful as an auxiliary catalyst for polymerization (e.g. Macromol. Chem. Rapid Commun. 2, PP 663–667, 1991).

Moreover, in the invention, the arylmagnesium halide are compounds represented by a general formula (II) of ArMgX. Here, Ar denotes an aryl group mentioned previously and X denotes halogen. Moreover, for the solvent to be used for arylmagnesium halide, a straight chain ether is preferable. Particularly preferable one is ethyl ether capable of being easily distilled off.

In the invention, usable boron trihalides include those represented by a general formula (III) of $BX_3$. Here, however, X is halogen. Further, coordinated compounds such as ethers, thioethers etc. of boron trihalide are also included therein. Since boron trichloride, boron tribromide and boron trifluoride have a low boiling point, compounds such as ethyl ether complex are easier to handle, so preferable.

In the method of the invention, a hydrocarbon type solvent or mixed solvent of hydrocarbon type solvent and straight chain ether type solvent are preferable as organic solvents inert to the reaction products. As the hydrocarbon type solvent, a saturated hydrocarbon type, aromatic type solvent, especially xylene, toluene and benzene give preferable results.

In the invention, particularly preferable results are obtained when the concentration of boron trihalide in the inert solvent is 0.1 to 8.0 mol/L and the concentration of arylmagnesium halide in an ether solvent, is 0.1 to 3.0 mol/L, because the concentration of the reaction mixture does not remarkably lower the productivity, also the density of the reaction mixture is not too high to disturb distilling-off of ether type solvent.

In the inventive reaction, when reacting boron trihalide with arylmagnesium halide, the boron trihalide is dissolved into an aromatic solvent, and a solution of the arylmagnesium halide in an ether type solvent is added dropwise to the boron trihalide solution.

At that time, the mixing temperature is desirable to be within a range from 15° to 65° C. If the mixing temperature is under 15° C., the triarylborane produced or magnesium salt produced as a by-product sometimes deposits as crystals hindering stirring. Also, if the mixing temperature is over 65° C., the yield drops in many cases. Moreover, the time for dropwise addition of arylmagnesium halide does not affect the yield of triarylborane.

In order to complete the reaction by removing ether from the reaction mixture, heating the reaction mixture at not less than 110° C. leads to improvement in reaction yield of triarylborane, further to improvements in recovering ratio by releasing triarylborane enclosed into magnesium salt while solidifying magnesium salt produced as a by-product and then to improvement in the reproductivity thereof.

The reaction pressure may be either atmospheric pressure or applied pressure by the use of autoclave. Considering that triarylborane is sensitive to oxygen and moisture, however, the reaction under applied pressure is more preferable in a sense of eliminating the influence thereof.

According to the invention, in the reaction of an aryl magnesium halide and boron trihalide, the aryl magnesium halide is used in an amount of 3.1 equivalent weight relative to the boron trihalide or a slight excess thereof, whereby it is possible to obtain highly pure stable triarylborane in high yield.

As shown in the comparative examples described later, if the use of arylmagnesium halide is less than 3.1 equivalent weight or in excess of the boron trihalide, the stability of triarylborane will become poor and the yield and purity will decrease. On the contrary, in the examples, stable highly pure triarylborane can be obtained in high yield.

In the invention, the significance of using a slight excess of arylmagnesium halide lies in not only the increased yield of triarylborane, but also the contribution to increased stability. This feature makes it possible to produce reproducible triarylborane on industrialization bringing about a large merit.

In the following, the invention will be illustrated in more detail based on the examples, but these are examples for illustration only and the invention is not subject to the restriction by following the examples.

The yield in following Examples 1 to 4 and Comparative examples 1 and 2 was determined by an internal reference method based on the boron trihalide using liquid chromatography after the boron trihalide is converted to a stable complex through the reaction with butyl lithium. Moreover, in Example 3 and Comparative example 3, the complex produced from butyl lithium was further derivitized to form the tetramethylammonium salt or N,N-dimethylanilinium salt to determine the yield from dry weight because of hygroscopicity and unstability, and further the yield and purity thereof were determined by internal reference method using fluorine nuclear magnetic resonance spectrum.

Especially in Example 3, the yield and the purity of triarylborane itself could be directly determined by internal reference method using fluorine nuclear magnetic resonance spectrum, of which values are described together.

EXAMPLE 1

A 200 mL glass three-neck round bottom flask was equipped with a 50 mL glass dropping funnel, and the internal air was replaced enough with nitrogen. And, 30 mL of xylene deaerated thoroughly with nitrogen and 2.78 g (0.0196 mol) of boron trifluoride ethyl ether complex were charged into the flask. Moreover, into the dropping funnel were charged 33.51 g (0.0647 mol) of 35 wt. % ethyl ether solution of phenylmagnesium bromide. The ether solution of phenylmagnesium bromide was added dropwise from the dropping funnel to the reactor under stirring. The reaction temperature at that time was from 18.6° to 29.9° C. After the completion of dropwise addition, the reactor was heated to remove ethyl ether.

After the temperature of reaction mixture has reached the boiling point, aging was performed for 1, 3 and 5 hours at that temperature and sample was taken at each time. After magnesium bromide fluoride was removed with glass filter, butyl lithium was added into the pale yellow transparent liquids and the yield was determined from compounds obtained as stable complexes, which showed 88.7%, 87.7% and 86.2%, respectively.

EXAMPLE 2

A 200 mL glass three-neck round bottom flask was equipped with a 50 mL glass dropping funnel, and the internal air was replaced enough with nitrogen. And, 30 mL of toluene deaerated enough with nitrogen and 2.78 g (0.0196 mol) of boron trifluoride ethyl ether complex were charged into the flask. Moreover, into the dropping funnel were charged 33.51 g (0.0647 mol) of 35 wt. % ethyl ether solution of phenylmagnesium bromide. The ethyl ether solution of phenylmagnesium bromide was added dropwise from the dropping funnel to the reactor under stirring. The reaction temperature at that time was from 18.6° to 29.9° C. After the completion of dropwise addition, the reactor was heated to remove ethyl ether.

After the temperature of the reaction mixture has reached the boiling point, heating was performed for 1, 3 and 5 hours at that temperature and sample was taken at each time. After magnesium bromide fluoride was removed with a glass filter, butyl lithium was added into the pale yellow transparent liquids and the yield was determined from compounds obtained as stable complexes, which showed 91%, 90.7% and 90.7%, respectively.

EXAMPLE 3

A 200 mL glass three-neck round bottom flask was equipped with a 50 mL glass dropping funnel, and the internal air was replaced with nitrogen. And, 30 mL of tolune deaerated thoroughly with nitrogen and 2.78 g (0.0196 mol) of boron trifluoride ethyl ether complex were charged into the flask. Moreover, into the dropping funnel were charged 84.99 g (0.0627 mol) of 20 wt. % ether solution of pentafluorophenylmagnesium bromide. The ethyl ether solution of pentafluorophenlmagnesium bromide was added dropwise from dropping funnel to the reaction mixture under stirring. The reaction temperature at that time was around 26° C. with little generation of heat. After the completion of dropwise addition, the reaction mixture was heated to remove ethyl ether.

After the temperature of the reaction mixture has reached the boiling point of toluene, heating was performed for 1 hour at that temperature and magnesium bromide fluoride was removed with a glass filter. The reaction mixture was dried with concentrating of the solvent, and the dried product was determined by fluorine nuclear magnetic resonance spectroscopy using pentafluorotoluene as an internal standard which gave the yield of 92%. Buthyl lithium was added into the light brown liquid and then an aqueous solution of trimethyl ammonium chloride was added. The dry weight of the compound thus obtained was 85% of theoretical value.

Then, another compound was obtained by, after reacting with pentafluorophenyl lithium prepared at −70° C. in a mixed solvent of ethyl ether-hexane from pentafluorophenyl bromide and butyl lithium instead of the above butyl lithium, adding an aqueous solution of N,N-dimethylanilinium chloride, of which dry weight was 85% of the theoretical value and the yield was determined to be 85% by fluorine nuclear magnetic resonance spectroscopy using pentafluorotoluene as an internal standard.

EXAMPLE 4

A 200 ml glass three-neck round bottom flask was equipped with a 50 ml glass dropping funnel, and the inside thereof was thoroughly replaced with nitrogen. Then, 30 ml of toluene which was thoroughly degassed with nitrogen and 2.78 g (0.0196 mol) of boron trifluoride ethyl ether complex were charged into the flask.

Then, into the dropping funnel was added ethyl ether solution 61.42 g (0.0619 mol) of 20% wt. ethyl ether solution of p-tolylmagnesium bromide. Into the flask was added the ethyl ether solution of p-tolylmagnesium bromide from the dropping funnel under stirring. The reaction temperature was about 20°–30° C., which was hardly exothermic. After completion of dropwise addition, the reaction mixture was heated to remove ethyl ether.

After the temperature of the reaction mixture reached the boiling point, it was subjected to heating at this temperature for three hours. After removal of magnesium bromide fluoride through a glass filter, the produced light yellow transparent liquid was added with butyl lithium to give a compound of stable complex, of which yield was determined to be 89.6% and purity was measured to be 91.6% in the areal percentage using liquid chromatography.

COMPARATIVE EXAMPLE 1

A 200 mL glass three-neck round bottom flask was equipped with a 50 mL glass dropping funnel, and the inside of system was replaced with nitrogen. And, 30 mL of toluene bubbled with nitrogen to deaerate thoroughly and 2.78 g (0.0196 mol) of boron trifluoride ethyl ether complex were charged into the flask. Moreover, into the dropping funnel were charged 30.83 g (0.0597 mol) of 35 wt. % ether solution of phenylmagnesium bromide. The ethyl ether solution of phenylmagnesium bromide was added dropwise from the dropping funnel to the reactor under stirring. After the completion of dropwise addition, the reactor was heated to remove ethyl ether.

After the temperature of the reaction mixture has reached the boiling point of solvent, samples were taken at 1, 3 and 5 hours of heating time. When determining the yield by the method described previously, it showed 90.0%, 86.5% and 83.8%, respectively, showing a decreasing trend in yield. Moreover, with an increase in aging time, increased by-product originating from fluorodiphenylborane was also recognized.

COMPARATIVE EXAMPLE 2

A 200 mL glass three-neck round bottom flask was equipped with a 50 mL glass dropping funnel, and the inside of system was replaced with nitrogen. And, 30 mL of toluene bubbled with nitrogen to deaerate thoroughly and 2.78 g (0.0196 mol) of boron trifluoride ethyl ether complex were charged into the flask. Moreover, into the dropping funnel were charged 38.23 g (0.0738 mol) of 35 wt. % ethyl ether solution of phenylmagnesium bromide. The ethyl ether solution of phenylmagnesium bromide was added dropwise from the dropping funnel to the reactor under stirring. After the completion of dropwise addition, the reaction mixture was heated to remove ethyl ether.

After the temperature of the reaction mixture has reached the boiling point of solvent, samples were taken at 1, 3 and 5 hours of heating time. When determining the yield by the method described previously, it showed low yields of 65.0%, 64.5% and 64.5%, respectively, but a decreasing trend was hardly recognized.

COMPARATIVE EXAMPLE 3

A 200 mL glass three-neck round bottom flask was equipped with a 50 mL glass dropping funnel, and the internal air was replaced with nitrogen. And, 30 mL of toluene deaerated throughly with nitrogen and 2.78 g (0.0196 mol) of boron trifluoride ethyl ether complex were charged into the flask. Moreover, into the dropping funnel were charged 79.67 g (0.0588 mol) of 20 wt. % ethyl ether solution of pentafluorophenylmagnesium bromide. The ethyl ether solution of pentafluorophenylmagnesium bromide was added dropwise from the dropping funnel to the reaction mixture under stirring. The reaction temperature at that time was around 26° C. with little generation of heat. After the completion of dropwise addition, the the reaction mixture was heated to remove ethyl ether.

After the temperature of the reaction mixture has reached the boiling point of toluene, heating was performed for 1 hour at that temperature and magnesium bromide fluoride was removed with a glass filter. Butyl lithium was added into the light brown liquid and then an aqueous solution of trimethylammonium chloride was added. The dry weight of the compound thus obtained was 65% of the theoretical value.

What is claimed is:

1. A method of producing a triarylborane, comprising the steps of:
   (1) reacting a 1.0–8.0 mol/L boron trihalide solution in an inert hydrocarbon or hydrocarbon/ether solvent with a 0.1–3.0 mol/L aryl magnesium halide solution in an ether solvent, where the molar ratio of aryl magnesium halide to boron trihalide is 3.1–3.5 to 1.0, respectively, to form a reaction mixture containing a triarylborane and a halogenated magnesium salt;
   (2) distilling said ether solvent from said reaction mixture; and
   (3) removing said halogenated magnesium salt from said mixture.

2. The method of claim 1, wherein said boron trihalide has the formula $BX_3$, wherein X is halogen, ether or thioether complexes thereof.

3. The method of claim 2, wherein said boron trihalide is boron trichloride, boron tribromide, boron trifluoride, ether or thioether complexes thereof.

4. The method of claim 3, wherein said boron trihalide is the ethyl ether complex.

5. The method of claim 1, wherein said hydrocarbon solvent is a saturated hydrocarbon or aromatic hydrocarbon.

6. The method of claim 5, wherein said hydrocarbon solvent is xylene, toluene or benzene.

7. The method of claim 1, wherein said reacting step is conducted at a temperature from 15°–65° C.

8. The method of claim 1, wherein the aryl group of said aryl magnesium halide is selected from the group consisting of phenyl, fluorophenyl, chlorophenyl, bromophenyl, methoxyphenyl, tolyl, xylyl, mesityl, biphenyl, naphthyl, pyridyl, trifluorphenyl, pentafluorophenyl, and tris(trifluoromethyl)phenyl.

9. The method of claim 8, wherein the phenyl group of said aryl magnesium halide is phenyl or tris(pentafluorophenyl).

10. The method of claim 1, wherein said ether is diethylether.

11. The method of claim 1, further comprising heating said reaction mixture together with distilling step (2) and then comprising, after removal of said ether solvent, heating said reaction mixture at the boiling temperature of said hydrocarbon for 1–5 hours prior to removing step (3).

* * * * *